United States Patent [19]

Kress et al.

[11] Patent Number: 4,776,981
[45] Date of Patent: Oct. 11, 1988

[54] FLAMEPROOFING AGENTS, THEIR PREPARATION AND THEIR USE FOR PROVIDING POLYCARBONATES WITH A FLAME-RESISTANT FINISH

[75] Inventors: Hans-Jürgen Kress, Krefeld; Klaus Kircher, Leverkusen, both of Fed. Rep. of Germany

[73] Assignee: Bayer Aktiengesellschaft, Bayerwerk, Fed. Rep. of Germany

[21] Appl. No.: 88,929

[22] Filed: Aug. 24, 1987

Related U.S. Application Data

[62] Division of Ser. No. 935,448, Nov. 26, 1986, Pat. No. 4,713,462, which is a division of Ser. No. 661,770, Oct. 17, 1984, Pat. No. 4,661,543.

[30] Foreign Application Priority Data

Oct. 18, 1983 [DE] Fed. Rep. of Germany ....... 3337857

[51] Int. Cl.$^4$ ................................................ C08K 5/34
[52] U.S. Cl. .................................. 252/609; 252/400.1; 252/400.23; 252/400.52; 252/402; 524/94; 524/148; 524/166; 524/415; 524/418
[58] Field of Search ................. 524/94, 148, 166, 415, 524/418; 252/400.1, 400.23, 400.52, 402, 609

[56] References Cited

U.S. PATENT DOCUMENTS

| | | | |
|---|---|---|---|
| 3,753,679 | 8/1973 | Singhal | 71/98 |
| 4,208,489 | 6/1980 | Schmidt et al. | 525/146 |
| 4,552,911 | 11/1985 | Cohnen et al. | 524/94 |
| 4,661,543 | 4/1987 | Kress et al. | 524/94 |

FOREIGN PATENT DOCUMENTS 0019126 4/1980 European Pat. Off. .
0019127 4/1980 European Pat. Off. .
2918882 11/1980 Fed. Rep. of Germany .
2918883 11/1980 Fed. Rep. of Germany .

OTHER PUBLICATIONS

Chemical Abstract, vol. 84, Jan. 1976, Nr. 84: 18389c p. 52.

Primary Examiner—Kriellion Morgan
Attorney, Agent, or Firm—Gene Harsh; Joseph C. Gil; Aron Preis

[57] ABSTRACT

The present invention relates to phthalimide compounds of the formula (I)

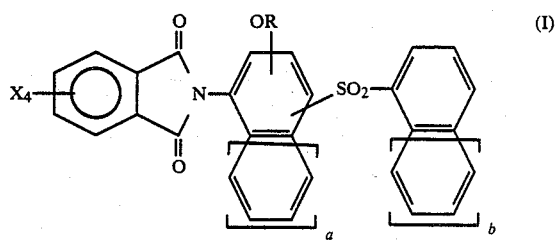

wherein
X denotes H or halogen, for example chlorine or bromine,
a and b independently of one another denote 0 or 1 and
R denotes a $C_1$–$C_4$-alkyl radical, which, in combination with alkali metal salts, are suitable as flameproofing agent combinations for thermoplastic, branched, aromatic polycarbonates, and the preparation of these compounds.

2 Claims, No Drawings

FLAMEPROOFING AGENTS, THEIR PREPARATION AND THEIR USE FOR PROVIDING POLYCARBONATES WITH A FLAME-RESISTANT FINISH

This application is a division of application Ser. No. 935,448 filed Nov. 26, 1986, now U.S. Pat. No. 4,713,462 which is a division of application Ser. No. 661,770 filed Oct. 17, 1984, now U.S. Pat. No. 4,661,543.

The present invention relates to phthalimide compounds of the formula (I)

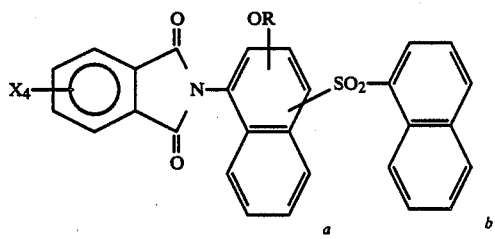

wherein

X denotes H or halogen, for example chlorine or bromine, a and b independently of one another denote 0 or 1 and R denotes a $C_1$–$C_4$-alkyl radical.

The present invention also relates to the preparation of phthalimides of the formula (I), which is characterised in that a phthalic anhydride of the formula (III)

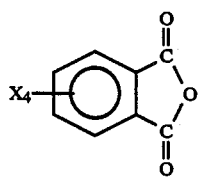

wherein

X has the meaning given in the case of formula (I), is reacted with an amine of the formula (II)

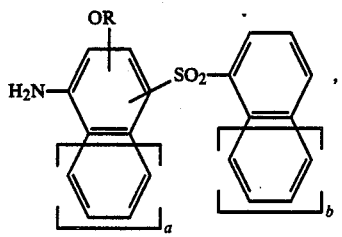

wherein

R, a and b have the meaning given in the case of formula (I), in equimolar amounts at 117° C., glacial acetic acid, as a solvent, and cyclohexane, as a water-entraining agent, also being used.

The amines of the formula (II) either are known from the literature (see, for example, U.S. Pat. No. 3,753,679) or can be obtained by the process described therein.

The amount of solvent to be used is about 2.5–3.0 liters per mole of amine employed; the amount of water-entraining agent is about 250–300 ml per mole of amine.

The new phthalimide compounds, in combination with the known flameproofing agents for polycarbonates, that is to say the alkali metal salts of organic or inorganic acids, are suitable synergists for improving the flame-repellency of thermoplastic aromatic polycarbonates prepared only from halogen-free phenolic components.

The present invention thus also relates to flameproofing agent combinations consisting of (a) 0.1 to 1 part by weight of a phthalimide of the formula (I) and (b) 0.02 to 2 parts by weight of an alkali metal salt of an organic or inorganic acid, in particular a sodium, potassium or lithium salt.

Alkali metal salts of organic or inorganic acids which are suitable as flameproofing agents are mentioned, for example, in German Offenlegungsschriften (German Published Specifications) No. 2,703,710, No. 2,918,882 and No. 2,918,883.

The present invention also relates to the use of the flameproofing agent combination according to the invention for providing thermoplastic, branched, aromatic polycarbonates of halogen-free phenolic components with a flame-repellent finish, in amounts of 0.1 to 1% by weight, based on the thermoplastic aromatic polycarbonate, of phthalimide of the formula (I) and 0.02 to 2% by weight, based on the thermoplastic, branched, aromatic polycarbonate, of alkali metal salt of an organic or inorganic acid.

The present invention furthermore relates to a process for providing thermoplastic, branched, aromatic polycarbonate of halogen-free phenolic components with a flame-repellent finish, which is characterised in that the flameproofing agents are incorporated by mixing and subsequent granulation via a twin-screw extruder at a material temperature of 270°–300° C., preferably 270°–280° C.

The optimum processing conditions are such that a throughput of 18 kg/hour is achieved at a speed of rotation of 40–80 revolutions/minute.

The twin-screw extruder used is a unit from Werner und Pfleiderer with the designation ZSK 53.

The present invention also relates to thermoplastic moulding compositions based on aromatic, branched, thermplastic polycarbonates of halogen-free phenolic components, containing 0.1 to 1% by weight of phthalimide of the formula (I) and 0.02 to 2% by weight of an alkali metal salt of an inorganic or organic acid, the two ranges of the percentages by weight each being based on the thermoplastic, branched, aromatic polycarbonate without other additives.

Aromatic, branched, thermoplastic polycarbonates of halogen-free phenolic components are to be understood as meaning that the diphenols, monophenols and trisphenols, tetraphenols or other branching agents to be used for the preparation of the polycarbonates do not have halogen substituents. These polycarbonates can, of course, still contain small residual ppm amounts of non-hydrolysed chlorine, for example if they are prepared by the phase boundary process using phosgene. In subsequenyt characterisation of the polycarbonates as "halogen-free", residues of halogen which can be hydrolysed in this way are not to be taken into consideration.

It is possible to obtain flameproofed polycarbonates with a UL 94 V-0 classification with the aid of these new flameproofing agents. Cl- and Br-free flameproofed polycarbonates with V-0 in a wall thickness of 1.6 mm can thus be obtained with the halogen-free phthalimides according to the invention. V-0 is also achieved in a wall thickness of 0.8 mm by using the halogen-containing compounds. In addition, the phthalimides of the formula (I) according to the invention are characterised by a low volatility under normal polycarbonate processing conditions.

The polycarbonate moulding compositions achieve a classification in burning class V-0, that is to say they do not drip and have an average after-burn time of less than 5 seconds, according to Underwriters' Laboratories Inc., Bulletin 94, Burning Tests for the Classification of Materials (called UL 94 below), on testpieces with dimensions of 127×12.7×3.2 mm (⅛") or 127×12.7×1.6 mm (1/16") or 127×12.7×0.8 mm (1/32").

It is known that the flame repellency of polycarbonates can be improved by addition of alkali metal salts, it being possible for the polycarbonates to be either halogen-free or halogen-substituted. (See, for example, DE-OS (German Published Specification) No. 1,930,257, DE-OS (German Published Specification) No. 2,049,358, DE-OS (German Published Specification) No. 2,112,987, DE-OS (German Published Specification) No. 2,149,311, DE-OS (German Published Specification) No. 2,253,072 and DE-OS (German Published Specifications) Nos. 2,458,968, 2,461,063, 2,461,146 and 2,461,077).

It is also known that the flame repellency of polycarbonates can be improved by mixtures of organic chlorine compounds and certain inorganic salts (see, for example, DE-OS (German Published Specification) No. 2,013,496; tetrachlorophthalic anhydride, inter alia, is mentioned as a suitable organic chlorine compound).

It is also known that polycarbonates can be rendered flame-repellent with brominated phthalimides (see U.S. Pat. No. 3,873,587).

It is also known that phthalimide compounds can be used in combination with alkali metal salt additives, exclusively halogenated phthalimides being employed (DOS (German Published Specification) No. 2,707,928, DOS (German Published Specification) No. 2,740,850 and DOS (German Published Specification) No. 2,703,710).

It is also known that organic halogen compounds, such as halogenated phthalimides, can be used in combination with alkali metal salts and with substances which reduce the tendency of polycarbonates to drip, for providing polymer blends based on polycarbonates with a flame-repellent finish. (See DE-OS (German Published Specification) No. 2,918,882 and DE-OS (German Published Specification) No. 2,918,883.)

It is also known that moulding compositions of branched aromatic polycarbonates can be provided with a flame-repellent finish for extreme flaming conditions together with alkali metal salts and halogenated phthalimides and an additional bromine content. (See DE-OS (German Published Specification) No. 3,203,905.)

However, in our opinion, the literature references mentioned neither anticipate nor suggest either the phthalimides of the formula (I) or their use as a flame-proofing synergist for halogen-free polycarbonates.

Furthermore, no additive combinations have hitherto been disclosed which, after admixing of such small amounts by weight of a chlorine-free and bromine-free phthalimide, already give polycarbonate moulding compositions of burning classes V 0 according to UL 94 at ⅛" and 1/16", and, using halogen-containing products, at 1/32" wall thickness.

The admixture claimed according to the invention of phthalimides of the general formula (I) is therefore particularly advantageous because compounds of these classes of substance are very stable to heat, have a low volatility, are stable to hydrolysis and can easily be mixed into polycarbonate.

Examples of suitable alkali metal salts of inorganic acids in the context of the invention are those of inorganic proton acids. Inorganic proton acids in the context of the invention are Brönsted acids which can form alkali metal salts (on the term "Brönsted) acid", compare Fieser & Fieser "Organic Chemistry", 1965, page 595, Interscience Publishers, N.Y., USA), such as, for example, meta-, ortho- and pyro-phosphoric acids and proton acids of complex fluorometallic compounds.

Suitable alkali metal salts of organic acids in the context of the invention are those of organic Brönsted acids with at least one carbon atom which can form alkali metal salts. Such optionally substituted organic acids can be OH- or NH-acid compounds, such as, for example, sulphonic acids, phosphonic acids, thiophosphonic acids and NH-acid sulphonamides or sulphonimides. They must have at least one C atom and can preferably contain between 2 and 30 C atoms.

The alkali metal salts which are suitable according to the invention hould preferably have a pH value of between 5 and 9, in particular between 6.5 and 7.5, measured on 1% strength by weight solutions or suspensions of the salts in water at 20° C.

Preferred alkali metal salts are the potassium, sodium and lithium salts, in particular the potassium salts.

Preferred alkali metal salts of organic acids are the sodium, potassium and lithium salts, but in particular the potassium salts of organic sulphonic acids and phosphonic acids, the organic radicals of which can be optionally substituted by halogens, such as fluorine, chlorine or bromine. Examples which may be mentioned are: sodium or potassium perfluorobutanesulphonate, sodium or potassium perfluoromethanesulphonate, sodium or potassium 2,5-dichlorobenzenesulphonate, sodium or potassium 2,4,5-trichlorobenzenesulphonate, sodium or potassium (4-chlorophenyl)phosphonate, sodium or potassium methyl-phosphonate, sodium or potassium (2-phenylethyl)-phosphonate and lithium phenyl-phosphonate.

Preferred alkali metal salts of inorganic acids are the sodium, potassium and lithium salts, but in particular the potassium salts of proton acid complexes, such as fluorometallic compounds, and of meta-, ortho or pyrophosphoric acids.

Examples which may be mentioned are: trisodium or tripotassium hexafluoroaluminate, disodium or dipotassium hexafluorotitanate, disodium or dipotassium hexafluorosilicate, disodium or dipotassium hexafluorozirconate, sodium or potassium pyrophosphate, sodium or potassium metaphosphate, sodium or potassium tetrafluoborate, sodium or potassium hexafluorophosphate and sodium, potassium or lithium phosphate.

Particularly suitable salts are: potassium or sodium perfluorobutanesulphonate, potassium or sodium 2,5-dichlorobenzenesulphonate, potassium or sodium 2,4,5-trichlorobenzenesulphonate, potassium hexafluoroaluminate, potassium pyrophosphate, potassium methyl-phosphonate, sodium hexafluoroaluminate and lithium phenyl-phosphonate.

Mixtures of the salts with one another are also suitable.

Halogen-free aromatic, branched, thermoplastic polycarbonates in the context of the present invention are polycondensates which can be obtained by reacting halogen-free diphenols, in particular dihydroxydiarylalkanes, with phosgene or diesters of carbonic acid, dihydroxydiarylalkanes in which the aryl radicals carry alkyl groups in the o- and/or m-position relative to the hydroxyl group also being suitable, in addition to the unsubstituted dihydroxydiarylalkanes; these polycondensates are branched by incorporation of between 0.05 and 2.0 mole % (based on the diphenols employed) of compounds which are trifunctional or more than trifunctional, for example those with three or more than three phenolic hydroxyl groups.

Polycarbonates of this type and their prparation are described, for example, in German Offenlegungsschriften (German Published Specifications) Nos. 1,570,533, 1,595,762, 2,116,974 and 2,113,347, British Patent Specification No. 1,079,821, U.S. Pat. No. 3,544,514 and German Offenlegungsschrift (German Published Specification) No. 2,500,092.

The halogen-free aromatic, branched, thermoplastic polycarbonates have weight-average molecular weights Mw of between 15,000 and 100,000, preferably between 20,000 and 80,000, determined by measurement of the relative viscosity in $CH_2Cl_2$ at 25° C. and a concentration of 0.5 g/100 ml, after appropriate calibration.

Examples of suitable halogen-free diphenols are hydroquinone, resorcinol, 4,4'-dihydroxydiphenyl, bis(hydroxy-phenyl)-alkanes, such as, for example, $C_1$–$C_8$-alkylene- or $C_2$–$C_8$-alkylidene-bisphenols, bis-(hydroxyphenyl)-cycloalkanes, such as, for example, $C_5$–$C_{15}$-cycloalkylene- or $C_5$–$C_{15}$-cycloalkylidene-bisphenols, and bis-(hydroxy-phenyl)sulphides, ethers, ketones, sulphoxides or sulphones, furthermore, $\alpha,\alpha'$-bis-(hydroxyphenyl)diisopropylbenzene and the corresponding nuclear-alkylated compounds. Polycarbonates based on 2,2-bis-(4-hydroxyphenyl)-propane (bisphenol A), 2,2-bis-(4-hydroxy-3,5-dimethylphenyl)-propane (tetramethylbisphenol A) or 1,1-bis(4-hydroxy-phenyl)-cyclohexane (bisphenol Z) and those based on trinuclear bisphenols, such as $\alpha,\alpha$-bis-(4-hydroxyphenyl)-p-diisopropylbenzene are preferred.

Other halogen-free diphenols which are suitable for the preparation of the polycarbonates are described in U.S. Pat. Nos. 3,028,365 and 3,275,601.

Examples of some of the compounds which have three or more than three phenolic hydroxy groups and which can be used are phloroglucinol, 4,6-dimethyl-2,4,6-tri-(4-hydroxyphenyl)-hept-2-ene, 4,6-dimethyl-2,4,6-tri-(4-hydroxyphenyl)-heptane, 1,3,5-tri-(4-hydroxyphenyl)-benzene, 1,1,1-tri-(4-hydroxyphenyl)-ethane, tri-(4-hydroxyphenyl)phenylmethane, 2,2-bis-/4,4-bis-(4-hydroxyphenyl)-cyclohexyl/propane, 2,4-bis-(4-hydroxyphenyl-isopropyl)phenol, 2,6-bis-(2'-hydroxy-5'-methyl-benzyl)-4-methylpheniol, 2-(4-hydroxyphenyl)-2-(2,4-dihydroxyphenyl)-propane, hexa(4-(4-hydroxyphenyl-isopropyl)-phenyl)-orthoterephthalic acid ester, tetra-(4-hydroxyphenyl)-methane, tetra-(4-(4-hydroxyphenyl-isopropyl)-phenoxy)-methane and 1,4-bis((4',4''-dihydroxytriphenyl)-methyl)-benzene. Some of the other trifunctional compounds are 2,4-dihydroxybenzoic acid, trimesic acid, cyanuric chloride, 3,3-bis-(4-hydroxyphenyl)-2-oxo-2,3-dihydroindole and 3,3-bis-(4-hydroxy-3-methylphenyl)-2-oxo-2,3-dihydroindole.

Suitable chain stoppers for regulating the molecular growthare, for example, in the known manner, phenol and alkylphenols, which are used in the known amounts.

The aromatic, branched, thermoplastic polycarbonates are prepared in a known manner, for example by the phase boundary process or by the process in homogeneous solution. The aromatic, thermoplastic polycarbonates can also be prepared by the known transesterification process.

Particularly preferred polycarbonates in the context of the present invention are branched polycarbonates based on bisphenol A with a branching agent content of 0.3 to 1.0 mole %, based on the moles of bisphenol A.

A suitable amine of the formula II is

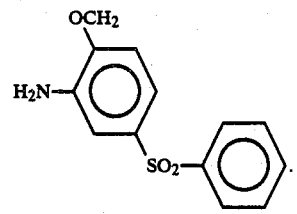

This compound is described in U.S. Pat. No. 3,753,679.

Suitable phthalimide compounds of the formula I are

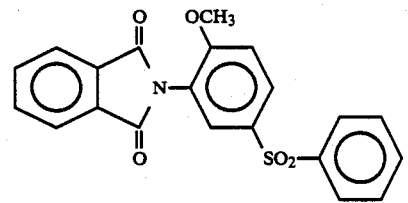

and

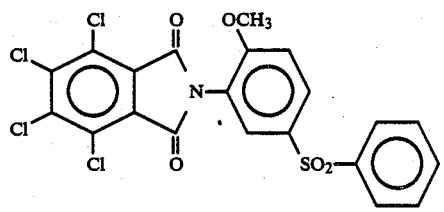

These compounds can be prepared by the process in the examples and under the general process conditions mentioned above.

The flameproofing agents according to the invention can be prepared beforehand by mixing the individual components or as a concentrate in the polycarbonate and stored until they are used.

The new flameproofing agent combination can be incorporated into the polycarbonates in the form of its individual components or as a whole, for example by mixing and subsequent granulation of the material via a twin-screw extruder at 270° to 280° C.

The moulding compositions according to the invention based on polycarbonate and flameproofing agent combination can also contain other additives customary in polycarbonate chemistry, such as, for example, pigments, dyestuffs, fillers, stabilisers or mould release agents.

The moulding compositions according to the invention can be processed to shaped articles or films.

Shaped articles are produced by the injection-moulding process at a temperature of 300°–310° C.

The moulding compositions according to the invention can be used, for example, in the electrical field for switch shields, sockets, socket panels, switchboxes and the like, in the domestic sector for housing components for irons and coffee machines and in the large appliance field, for example, for computer housing components.

Description of the burning test

According to the Ul 94 test (Underwriters's Laboratories, Inc.), polycarbonate samples are shaped to bars having dimensions of 127×12.7×3.2 (or 1.6 or 0.8) mm (5.00×0.5×⅛ (or 1/16 or 1/32) inches. The bars are mounted vertically so that the underside of the testpiece is 305 mm above a strip of bandaging material. Each test bar is ignited individually by means of two successive ignition operations lasting 10 seconds, the burning characteristics are observed after each ignition operation and the sample is then evaluated. A Bunsen burner with a 10 mm (⅜ inch) high blue flame of natural gas with a heat content of $3.73 \times 10^4$ kJ/m$^3$ 1.000 BTU per cubic foot) is used for igniting the sample.

The UL 94 V 0 classification concerns the properties, described below, of materials which have been tested in accordance with the UL 94 specification. The polycarbonates in this class contain no samples which burn for longer than 10 seconds after each section of the test flame; they show no total flaming time of more than 50 seconds on two actions of the flame on each set of samples; they contain no samples which burn completely up to the holding clamp attached at the top end of the sample; they contain no samples which ignite the cottonwool placed below the sample by burning drops or particles; they also contain no samples which glow for longer than 30 seconds after the test flame has been removed.

Other UL 94 classifications designate samples which are less flame-repellent and self-extinguishing and which give flaming drops or particles. These classifications are designated UL 94 V 1 and V-2.

The polycarbonates within the scope of this invention characteristically show the properties required for UL94 V-0 classification.

EXAMPLES

A. Preparation of phthalimides of the formula (I)

A.1 Preparation of a phthalimide of the general formula (I) using tetrachlorophthalic anhydride 1,600 ml of glacial acetic acid are initially introduced into a three-necked flask provided with a thermometer, stirrer and water separator, and are warmed to 55° C. A mixture of 171.6 g (0.6 mole) of tetrachlorophthalic anhydride and 157.8 g (0.6 mole) of 3-amino-4-methoxydiphenyl sulphone is then added and the mixture is stirred vigorously. The reaction mixture is kept under reflux at 118° C. for 2.5 hours and is then cooled. After addition of 150 ml of cyclohexane, the reaction mixture is kept under reflux for 6 hours, during which the water of reaction can be removed in the water separator.

The resulting solid is filtered off hot with suction, rinsed with glacial acetic acid, suspended in hot acetone and dried.

% N theory: 2.64; % C theory: 47.5; % H theory: 2.1. % Cl theory: 26.7. % N found: 2.86; % C found: 47.5; % H found: 2.05. % Cl found: 26.5.

A.2 Preparation of a phthalimide of the general formula (I) using phthalic anhydride The phthalimide is prepared according to A 1, using phthalic anhydride.

% N theory: 3.56; % C theory: 64.1; % H theory: 3.82. % N found: 3.54; % C found: 64.0; % H found: 3.84.

B. Flame-repellent, branched polycarbonates

A branched polycarbonate based on bisphenol A, 0.5 mole % of 3,3-bis-(4-hydroxy-3-methylphenyl)-2-oxo-2,3-dihydroindole, 3.0 mole % of phenol, as a chain stopper, and phosgene having a solution viscosity of 1.31 (measured in CH$_2$Cl$_2$ at 25° C. and in a concentration of 0.5 g/100 ml) was mixed with 0.1% of the K salt of n-perfluorobutanesulphonic acid or with the phthalimides according to the invention and the mixture was extruded and its fire repellency was examined according to UL 94 in thicknesses of 3.2 mm, 1.6 mm and 0.8 mm.

The following table shows the result:

| Examples: | | | | | | |
|---|---|---|---|---|---|---|
| PC (B) % | PFS % | PI % | Cl PI % | UL 94 V | | |
| | | | | 3.2 mm | 1.6 mm | 0.8 mm |
| 99.9 | 0.1 | | | V-0 | V-2 | V-2 |
| 99.4 | 0.1 | 0.5 | | V-0 | V-0 | V-2 |
| 99.4 | 0.1 | | 0.5 | V-0 | V-0 | V-0 |

PC (B): polycarbonate according to Example B
PFS: K salt of n-perfluorobutanesulphonic acid
PI: phthalimide based on 3-amino-4-methoxy-diphenyl sulphone according to A.2
Cl PI: tetrachlorophthalimide based on 3-amino-4-methoxy-diphenyl sulphone according to A.1

We claim:

1. A flame proofing agent combination consisting of 0.1 to 1 part by weight of a phthalimide of the general formula

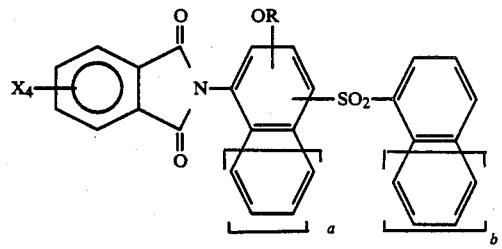

wherein
X denotes hydrogen or up to 4 halogen atoms,
a and b independently of each other denote 0 or 1, and
R denotes a C$_1$–C$_4$ alkyl radical, and
0.02 to 2 parts by weight of an alkali metal salt of an organic or inorganic acid.

2. A flameproofing agent according to claim 1, in which the salt of component (b) is selected from one or more of potassium or sodium perfluorobutanesulphonate, potassium or sodium 2,5-dichlorobenzenesulphonate, potassium or sodium 2,4,5-trichlorobenzenesulphonate, potassium hexafluoroaluminate, potassium pyrophosphate, potassium methyl-phosphonate, sodium hexafluoroaluminate and lithium phenyl-phosphonate.

* * * * *